United States Patent
Stanzione

(10) Patent No.: US 12,425,017 B2
(45) Date of Patent: Sep. 23, 2025

(54) POWER-ON RESET CIRCUITRY, AN IMPLANT DEVICE AND A METHOD FOR GENERATING A POWER-ON RESET SIGNAL

(71) Applicant: Stichting IMEC Nederland, Eindhoven (NL)

(72) Inventor: Stefano Stanzione, Veldhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 0 days.

(21) Appl. No.: 18/521,237

(22) Filed: Nov. 28, 2023

(65) Prior Publication Data
US 2024/0178833 A1 May 30, 2024

(30) Foreign Application Priority Data
Nov. 30, 2022 (EP) .................... 22210609

(51) Int. Cl.
| | | |
|---|---|---|
| G06F 1/24 | (2006.01) | |
| A61N 1/378 | (2006.01) | |
| H03K 17/22 | (2006.01) | |
| H03K 19/20 | (2006.01) | |
| H02J 50/00 | (2016.01) | |

(52) U.S. Cl.
CPC ......... *H03K 17/223* (2013.01); *A61N 1/3787* (2013.01); *G06F 1/24* (2013.01); *H03K 19/20* (2013.01); *H02J 50/00* (2016.02)

(58) Field of Classification Search
CPC .......... H03K 5/22; H03K 5/24; H03K 5/2472; H03K 5/2481; H03K 17/22; H03K 17/223; H03K 19/20; G06F 1/24; A61N 1/3787; H02J 50/00
See application file for complete search history.

(56) References Cited

U.S. PATENT DOCUMENTS

| | | |
|---|---|---|
| 5,485,111 A | 1/1996 | Tanimoto |
| 5,850,156 A | 12/1998 | Wittman |
| 6,737,884 B2 | 5/2004 | Shigemasa et al. |
| 6,879,194 B1 | 4/2005 | Caldwell |

(Continued)

FOREIGN PATENT DOCUMENTS

| | | |
|---|---|---|
| EP | 0999493 A2 | 5/2000 |
| WO | WO-2021/126724 A1 | 6/2021 |

OTHER PUBLICATIONS

Extended European Search Report for Application No. EP-22210609.8 dated May 10, 2023.

*Primary Examiner* — Long Nguyen
(74) *Attorney, Agent, or Firm* — MOSER TABOADA

(57) ABSTRACT

A power-on reset, POR, circuitry comprises: a comparator configured to output a POR trigger signal in dependence of a relation between a supply voltage and a target voltage level, wherein the comparator comprises a first output part configured to receive a balanced input; a trust unit comprising a second output part forming a replica of the first output part and configured to receive an unbalanced input, wherein the comparator and the trust unit are arranged in a common integrated circuit and wherein the trust unit is configured to output a trust signal indicating whether the POR trigger signal is trustable; and a decision unit configured to output a POR signal in dependence of the POR trigger signal and the trust signal.

15 Claims, 3 Drawing Sheets

(56) References Cited

U.S. PATENT DOCUMENTS

| | | |
|---|---|---|
| 8,547,144 B2 | 10/2013 | Lee et al. |
| 10,069,491 B2 | 9/2018 | Song et al. |
| 2017/0095206 A1* | 4/2017 | Leib .................. A61B 5/14542 |
| 2017/0237426 A1* | 8/2017 | Draxelmayr ......... H03K 17/223 |
| | | 327/143 |

* cited by examiner

POWER-ON RESET CIRCUITRY, AN IMPLANT DEVICE AND A METHOD FOR GENERATING A POWER-ON RESET SIGNAL

CROSS-REFERENCE TO RELATED APPLICATIONS

The present application claims the benefit of and priority to EP Patent Application Serial No. 22210609.8, filed Nov. 30, 2022, the entire contents of which is incorporated herein by reference.

TECHNICAL FIELD

The present description relates to a power-on reset circuitry and a method for generating a power-on reset signal. The present description also relates to an implant device comprising the power-on reset circuitry.

BACKGROUND

Integrated circuits commonly use a power-on reset (POR) signal. The POR signal may control reset of a circuit with memory to a known state after a system including the circuit starts up. The POR signal may need to be produced in a reliable manner in order to ensure reliable function of the system.

The system may need a settling time for a supply voltage to reach a settled voltage level after start-up. If the POR signal is provided to a circuit before the supply voltage has settled, the system may exhibit a buggy behavior. It may be particularly difficult to generate the POR signal in a reliable manner if the system has a slow or unpredictable rise of the supply voltage.

A POR circuitry for generating a POR signal may comprise a comparator which is configured to compare a scaled version of the supply voltage with a reference voltage. This may be useful in particular when the POR signal has a slow or unpredictable rise. However, at start-up, when a bias current of the comparator may be low, an output from the comparator may not necessarily be trusted in that its output could be high even if the scaled version of the supply voltage is not correctly larger than the reference voltage.

In particular, there is a need for providing a reliable POR signal that is correctly generated in relation to settling of supply voltage in a low power consumption system.

SUMMARY

An objective of the present description is to enable generation of a POR signal in a reliable manner. A particular objective of the present description is to enable generation of the POR signal using circuitry with low power consumption.

These and other objectives are at least partly met by the invention as defined in the independent claims. Preferred embodiments are set out in the dependent claims.

According to a first aspect, there is provided a power-on reset (POR) circuitry comprising: a comparator configured to compare a first voltage based on supply voltage to a reference voltage, wherein the comparator is configured to output a POR trigger signal in dependence of a relation between the supply voltage and a target voltage level, wherein the comparator comprises a first output part configured to receive a balanced input; a trust unit comprising a second output part forming a replica of the first output part and configured to receive an unbalanced input, wherein the comparator and the trust unit are arranged in a common integrated circuit and wherein the trust unit is configured to output a trust signal representing an indication whether the POR trigger signal is a trustable representation of the supply voltage reaching the target voltage level; and a decision unit configured to receive the POR trigger signal and the trust signal and configured to output a POR signal in dependence of the POR trigger signal and the trust signal.

The POR circuitry according to the first aspect is configured to use input from a comparator and from a trust unit in order to determine whether an indication of the comparator that supply voltage has increased such that a POR trigger signal should be generated can be trusted. Thus, the POR circuitry enables avoiding incorrect POR signals to be generated when the output of the comparator is unreliable. In particular, the output of the comparator may not be reliable when a biasing current of the comparator has not reached a normal operational level.

The first output part of the comparator of the POR circuitry may comprise a first node that receives a current based on comparison of the supply voltage to the reference voltage. The first node may further be connected to the supply voltage ($V_{dd}$) via a first component defining a first small signal equivalent resistance (hereinafter referred to as a first resistance) and to ground via a second component defining a second small signal equivalent resistance (hereinafter referred to as a second resistance). The first output part may receive a balanced input in that output of comparison between the supply voltage and the reference voltage is connected at opposite sides of the first node and defines a net current flowing into the first node.

It is an insight of the first aspect that, at start-up, the net current defined by the balanced input may be close to zero. Then, a voltage at the first node of the output part may instead be defined by any difference between the first resistance and the second resistance. Thus, it is an insight of the first aspect that an unbalance between the first resistance and the second resistance could cause the voltage at the first node of the output part to go from ground to $V_{dd}$ or vice versa, which could provide a false indication that a POR signal is to be generated.

The POR circuitry therefore comprises a trust unit, which comprises a second output part forming a replica of the first output part. The second output part may thus match the first output part and provides an indication whether the POR trigger signal from the comparator is generated based on the supply voltage truly reaching a sufficient level or whether the POR trigger signal from the comparator is generated based on an unbalance at the node of the output part.

The second output part may thus comprise a second node corresponding to the first node of the first output part. Like the first node of the first output part, the second node of the second output part may be connected to the supply voltage ($V_{dd}$) via a third component defining a third small signal equivalent resistance (hereinafter referred to as a third resistance) and to ground via a fourth component defining a fourth small signal equivalent resistance (hereinafter referred to as a fourth resistance). The third component of the second output part may be identical to the first component of the first output part whereas the fourth component of the second output part may be identical to the second component of the first output part.

The second output part further receives an unbalanced input. This implies that the second node of the second output part could be connected at one side of the second node (corresponding to the side of the third component or the side of the fourth component) to receive a current based on a relation between the supply voltage and the reference voltage. The current may be formed using a corresponding comparison as done by the comparator connected to the first output part. This implies that, when the supply voltage has reached a sufficient voltage, the voltage at the first node and the voltage of the second node are both controlled by the current based on comparison of the supply voltage and the trust unit may provide an indication that the POR trigger signal from the comparator may be trusted. On the other hand, when supply voltage is low, the voltage of the second node of the second output part is controlled in the same manner as the voltage of the first node of the first output part such that the trust unit may provide an indication the POR trigger signal from the comparator may not be trusted.

Thanks to the trust unit and the comparator being arranged in a common integrated circuit, components of the first output part and the second output part may be formed in parallel, ensuring that the components function correspondingly. This means that process, voltage, and temperature variations of the components should be minimal such that the trust unit may provide the trust signal based on a corresponding functionality of the second output part compared to the first output part. This implies that the trust signal may definitely provide an indication whether the POR trigger signal may be trusted.

The POR circuitry may be configured to sense a power applied to an integrated circuit and to generate an impulse signal that may generate a reset of the integrated circuit to place the integrated circuit in a known state. The POR circuitry may thus be configured to output a POR signal, which turns from low to high when reset of the integrated circuit is desired. It should be realized that the POR signal may alternatively be arranged such that it turns from high to low when reset of the integrated circuit is desired.

The comparator is configured to output a POR trigger signal. This should be understood as a signal which is used for controlling whether the POR signal is to be output. The POR trigger signal may turn from low to high (or from high to low, depending on implementation) when the comparator senses that power is applied to the integrated circuit. However, as explained above, the POR trigger signal may also incorrectly turn from low to high. Therefore, according to the first aspect, the output of the comparator is not directly used as a POR signal for resetting the integrated circuit. Rather, the output of the comparator goes via the decision unit in order to determine whether the output of the comparator, the POR trigger signal, can be trusted and to, based on this decision, output the POR signal.

The comparator may compare a first voltage based on supply voltage to a reference voltage. This implies that the comparator may not necessarily directly compare the supply voltage to the reference voltage. Rather, the comparator may be configured to receive a scaled version of the supply voltage forming the first voltage, which is then compared to the reference voltage. It should be realized that the first voltage may be formed in different manners based on the supply voltage, such as the first voltage being a scaling of the supply voltage, or even that the first voltage corresponds directly to the supply voltage.

The comparator may be configured to output the POR trigger signal in dependence of a relation between the supply voltage and a target voltage level. The target voltage level may correspond to or be close to a settled voltage of the supply voltage after a rise of the supply voltage.

The second output part of the trust unit forms a replica of the first output part in that the second output part is formed by same components connected in the same way as the first output part. As discussed above, the first output part may comprise a first and a second component connected to a first node and the second output part may correspondingly comprise a third and a fourth component connected to a second node. However, it should be realized that a layout of the first output part and the second output part may be different. For instance, further components may be present.

According to an embodiment, the first, second, third and fourth components may be transistors.

The first output part being configured to receive a balanced input implies that the first output part is connected to receive input at opposite sides of a node, wherein input currents at opposite sides of the node are inverted (equal value and in opposite directions) in relation to each other.

The second output part being configured to receive an unbalanced input implies that the second output part may receive input only at one side of a node or that the second output part receives inputs at opposite sides of the node where input currents are not of equal value.

The decision unit may be any unit that is able to determine an output in dependence of receiving the POR trigger signal and the trust signal. For instance, the decision unit may be simply formed as a logic gate, such as an AND gate. Alternatively, the decision unit may be a more complex structure, such as comprising a plurality of logic gates.

According to an embodiment, the comparator further comprises a first input transconductor part configured to generate a current to the first output part.

The first transconductor part may be configured to generate a current in relation to a difference between the first voltage and the reference voltage. Thus, the first transconductor part may suitably be used for comparing the first voltage and the reference voltage.

The first transconductor part and the output part may be arranged such that an output from the first transconductor part is received by the output part, which may further provide an output for forming the POR trigger signal. The first transconductor part may be form a transconductor stage of the comparator and the output part may form an output stage of the comparator, following the transconductor stage.

According to an embodiment, the first input transconductor part is configured to receive the first voltage and the reference voltage as input signals to the comparator.

The first transconductor part may form a differential input transconductor, wherein the first voltage and the reference voltage are received as a differential input.

In particular, the first transconductor part may generate the current as a function of a difference between the first voltage and the reference voltage. Thus, the first transconductor part may provide a current that represents a relation between the first voltage and the reference voltage, which further allows the comparator to output the POR trigger signal in dependence of the relation between the first voltage and the reference voltage.

According to an embodiment, the trust unit comprises a second transconductor part at a negative side of the unbalanced input.

The second transconductor part may be configured to provide a negative current at the negative side of the unbalanced input to the second output part, wherein the negative current is formed in dependence of the supply voltage. The second transconductor part may thus ensure that a voltage at the second node of the second output part is always low when the supply voltage has settled.

As mentioned above, when the supply voltage is low, the voltage of the second node of the second output part is controlled in the same manner as the voltage of the first node of the first output part. The second transconductor part providing unbalanced input at the negative side of the second node may further ensure that, if there is an unbalance between the components of the first output part, the same unbalance between the components of the second output part may reliably be used to generate a trust signal that provides a representation whether the POR trigger signal may be trusted.

It should be realized that, in dependence of a logic used by the decision unit, the output of the second output part may need to be inverted before reaching the decision unit to correctly represent whether the POR trigger signal can be trusted. For instance, if the decision unit uses an AND gate, the signal output by the second output part may need to be inverted, when the second transconductor part is arranged at a negative side of the unbalanced input of the second output part.

However, it should be realized that the trust unit may instead comprise a transconductor part at a positive side of the unbalanced input. In such case, the trust unit may still provide a trust signal which reliably provides an indication whether the POR trigger signal may be trusted. The output of the second output part may however not need to be inverted in relation to the POR trigger signal.

According to an embodiment, the second transconductor part is configured to receive a supply voltage at a negative input and ground at a positive input.

This implies that it may be ensured that the second transconductor part may ensure a maximum unbalance of the second output part, such that if the first output part is unbalanced to provide a signal that is high at the first node, the second output part will surely also generate a signal that is high at the second node. This may provide a reliable output of the second output part which may be used for providing a reliable trust signal.

According to an embodiment, the first output part is configured to output a signal to at least one inverter of the comparator, wherein the comparator is configured to output the POR trigger signal from the at least one inverter of the comparator.

According to an embodiment, the second output part is configured to output a signal to at least one inverter of the trust unit, wherein the trust unit is configured to output the trust signal from the at least one inverter of the trust unit.

The inverters imply that an input of the decision unit may be decoupled from the first and second output parts. The comparator as well as the trust unit do not consume much power, which implies that they have high impedance.

The inverters may ensure that, if the POR trigger signal or the trust signal flips, no charge is capacitively transferred via the decision unit to the other output part. Such charge transfer could otherwise cause a change of state of the output part receiving the charge so that the POR signal may not be generated correctly.

According to an embodiment, a number of inverters of the at least one inverter of the comparator is even and a number of inverters of the at least one inverter of the trust unit is odd or the number of inverters of the at least one inverter of the comparator is odd and the number of inverters of the at least one inverter of the trust unit is even.

Thus, the inverters of the comparator and the trust unit may be arranged such that an odd number of inverters and an even number of inverters are used. This implies that, if the voltage at the second node of the second output part of the trust unit is low when the voltage at the first node of the comparator is high, when the supply voltage has settled, the trust signal and the POR trigger signal may be ensured to both be low or both be high. This facilitates a simple implementation of the decision unit to reliably generate the POR signal.

According to an embodiment, the decision unit comprises an AND gate or a NOR gate configured to receive the POR trigger signal and the trust signal and configured to output the POR signal.

This implies that the decision unit is formed by a small and simple logic. The AND gate may be used if the POR trigger signal and the trust unit are configured to both be high when the POR signal is to be generated, whereas the NOR gate may be used if the POR trigger signal and the trust unit are configured to both be low when the POR signal is to be generated.

According to a second aspect, there is provided an implant device comprising the POR circuitry according to the first aspect, wherein the implant device is configured to be implanted in a body and configured to receive power through wireless power transfer for causing generation of the POR signal by the POR circuitry.

Effects and features of this second aspect are largely analogous to those described above in connection with the first aspect. Embodiments mentioned in relation to the first aspect are largely compatible with the second aspect.

The POR circuitry may be particularly suitable for use in an implant device which may be powered through wireless power transfer. The wireless power transfer to the implant device may be subject to dynamically changing conditions, depending on a relation between the implant device and a power source. The implant device may for instance be powered by a power source arranged externally to the body. This implies that the implant device may not start-up in the same manner every time and that a settling time for the supply voltage may differ substantially.

Thanks to using the POR circuitry in the implant device, the POR signal may be generated in a reliable manner to ensure a proper functionality of the implant device even though the settling time of the supply voltage during start-up may vary between different start-up occasions.

The implant device may be configured to be implanted in a human body or an animal body.

According to a third aspect, there is provided a method for generating a power-on reset (POR) signal, comprising: comparing, by a comparator, a first voltage based on supply voltage and a reference voltage to output a POR trigger signal in dependence of a relation between the supply voltage and a target voltage level, wherein the comparator comprises a first output part configured to receive a balanced input; generating, by a trust unit, a trust signal representing an indication whether the POR trigger signal is a trustable representation of the supply voltage reaching the target voltage level, wherein the trust unit comprises a second output part forming a replica of the first output part and configured to receive an unbalanced input, wherein the comparator and the trust unit are arranged in a common integrated circuit; and outputting, by a decision unit, a POR signal in dependence of the POR trigger signal and the trust signal.

Effects and features of this third aspect are largely analogous to those described above in connection with the first and second aspects. Embodiments mentioned in relation to the first and second aspects are largely compatible with the third aspect.

Thanks to the trust unit, the method may generate the POR signal in a reliable manner in relation to the supply voltage.

BRIEF DESCRIPTION OF THE DRAWINGS

The above, as well as additional objects, features, and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
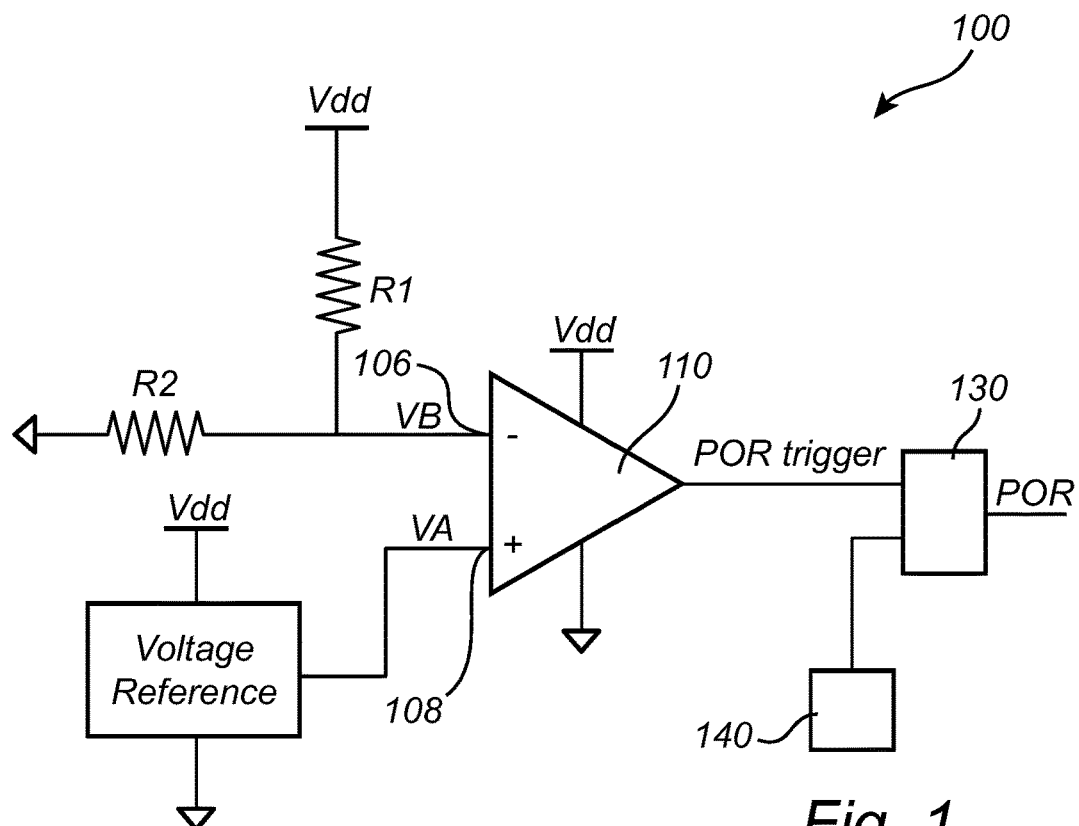
FIG. 1 is a schematic view of a power-on reset (POR) circuitry according to an embodiment.

Referring now to FIG. 1, a power-on reset (POR) circuitry 100 according to an embodiment will be generally described.

The POR circuitry 100 comprises a comparator 110. The comparator is configured to compare a first voltage based on supply voltage to a reference voltage. Thus, the comparator 110 is configured to receive a first voltage VB at a first input 106 of the comparator 110 and to receive a reference voltage VA at a second input 108 of the comparator 110.

The first voltage may be a scaled version of supply voltage. As shown in FIG. 1, the first voltage may be provided at a node arranged between resistances R1 and R2, wherein resistance R1 is further connected to the supply voltage and resistance R2 is further connected to ground. This implies that the first voltage provided to the first input 106 of the comparator 110 will be $VB=V_{dd}*R2/(R1+R2)$.

The reference voltage may also be dependent on the supply voltage. The reference voltage and the first voltage may be arranged such that when a system is starting up and the supply voltage is rising towards a target voltage level, the reference voltage will initially be lower than the first voltage and may become larger than the first voltage when the supply voltage has reached the target voltage level. The target voltage level may correspond to a settled voltage level of the supply voltage or close to a settled voltage level.

The comparator 110 may thus provide an output when the reference voltage exceeds the first voltage, which may be used for triggering a POR signal. The POR signal may control reset of a circuit with memory to a known state after a system including the circuit starts up. The POR signal should be provided quickly at start-up to ensure that the system fully starts up quickly. However, the POR signal should not be provided too early such that the supply voltage has not settled when circuit(s) are reset, since this may imply that the resetting is not properly performed and may cause incorrect behavior of the circuit(s). When a supply voltage rises slowly or unpredictably, it may be particularly difficult to provide the POR signal at a correct moment in time.

Thanks to comparing the first voltage to the reference voltage, the POR circuitry 100 may be able to determine when the supply voltage is close to or has reached the target voltage level. This implies that, regardless of how the supply voltage rises to the target voltage level, the POR signal may be provided when the target voltage level is reached such that the circuit(s) may be properly reset when the POR signal is received.

However, the comparator 110 will be arranged to compare voltages in a range from 0V to the target voltage level. Even though the reference voltage and the first voltage may be provided such that the reference voltage only exceeds the first voltage when the supply voltage is close to or has reached the target voltage level, the comparator 110 should also correctly determine the relation between the reference voltage and the first voltage over the entire range. This is particularly challenging, since transistors of the comparator 110 will move across different operating regions during rise of the supply voltage and in a range of 0V to a few hundred mV, the transistors will be not only under threshold, but also biased with a very small current. Hence, output of the comparator 110 may not necessarily be trusted, in particular when the supply voltage is close to 0V. Thus, there is a risk that the comparator 110 may incorrectly indicate that the reference voltage is larger than the first voltage before the supply voltage has reached the target voltage level.

The POR circuitry 100 comprises a decision unit 130, which is configured to receive a POR trigger signal from the comparator 110. The comparator 110 outputs the POR trigger signal when the reference voltage exceeds the first voltage indicating that the supply voltage is close to or has reached the target voltage level. However, the comparator 110 may also incorrectly output the POR trigger signal due to the comparator 110 not operating correctly, e.g., when the supply voltage is close to 0V, as explained above.

The POR circuitry 100 further comprises a trust unit 140 which may be configured to output a trust signal to the decision unit 130, the trust signal representing an indication whether the POR trigger signal from the comparator 110 may be trusted. The decision unit 130 may thus receive the POR trigger signal from the comparator 110 and the trust signal from the trust unit 140 and may output a POR signal in dependence of the POR trigger signal and the trust signal such that the POR signal may be provided in a reliable manner.

Figure 2:
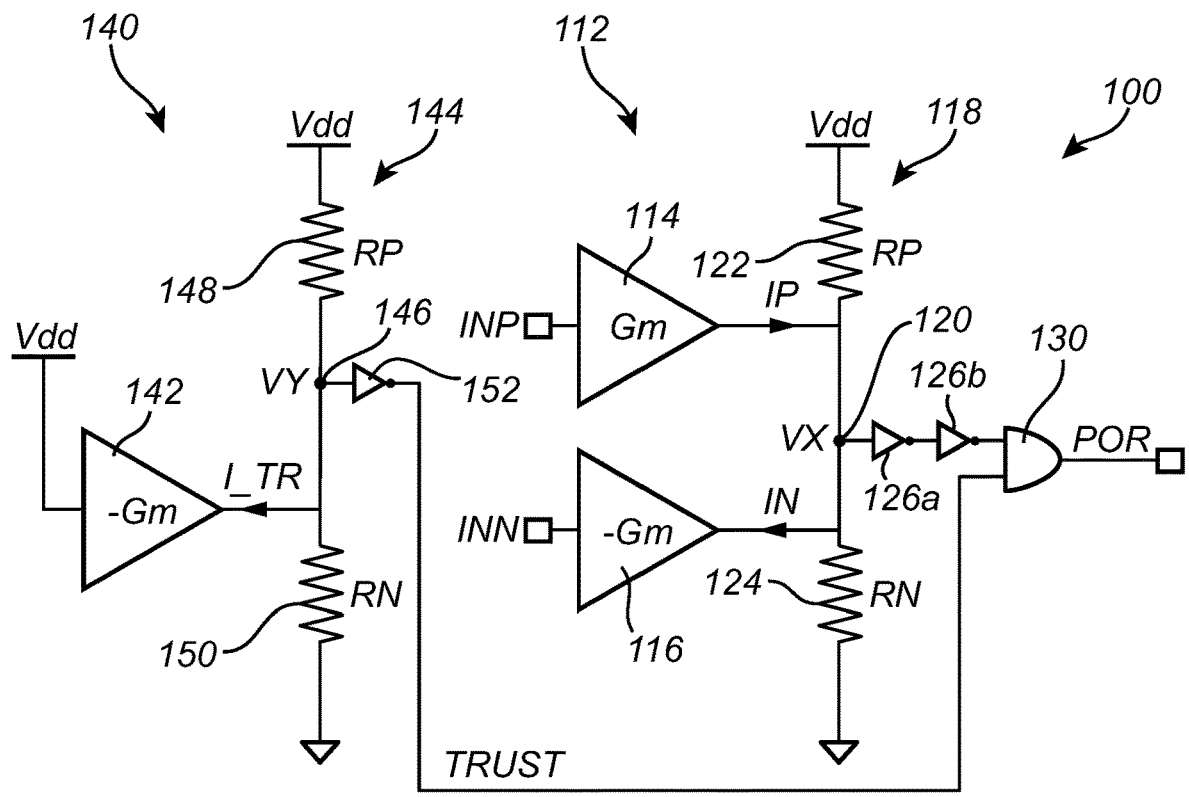
FIG. 2 is a more detailed schematic view of the POR circuitry.

Referring now to FIG. 2, the POR circuitry 100 will be described in further detail, while explaining a reason why the comparator 110, according to an insight of the present description, may incorrectly output the POR trigger signal at low levels of the supply voltage will be further described.

As illustrated in FIG. 2, the comparator 110 may comprise a first transconductor part 112 and a first output part 118. The first transconductor part 112 may be referred to as a transconductor stage and the output part may be referred to as an output stage of the comparator 110.

The comparator 110 may be configured to receive a differential input, receiving input signals INP and INN. The first transconductor part 112 may comprise a positive transconductor part 114 and a negative transconductor part 116. The positive transconductor part 114 is arranged to receive the input signal INP and configured to provide a current IP into a first node 120 of the first output part 118 at a positive side of the node 120 (a side connected to supply voltage). The negative transconductor part 116 is arranged to receive the input signal INN and configured to provide a current IN into the first node 120 of the first output part 118 at a negative side of the node 120 (a side connected to ground).

The positive transconductor part 114 and the negative transconductor part 116 provide a balanced input to the first output part 118 in that input currents to the first node 120 in relation to the positive transconductor part 114 and the negative transconductor part 116 are inverted (equal value and in opposite directions). Thus, a net current flowing into the first node 120, which is a node at which an output signal is provided, is equal to IP−IN=Gm*(INP−INN), wherein Gm is a transconductance of the positive transconductor part 114 and the negative transconductor part 116, respectively.

The first node 120 may be connected to the supply voltage via a first component 124 having a first resistance RP. The first component 122 may be formed by one or more transistors. The first node 120 may further be connected to ground via a second component 124 having a second resistance RN. The second component 124 may be formed by one or more transistors.

If a direct current (DC) operating point of the comparator 110 is correctly designed, RP is approximately equal to RN. Both resistances may be very large such that it is sufficient to have a small unbalance between the first input 106 and the second input 108 of the comparator 110 in order to move a voltage at the first node 120 from ground to Vdd or vice versa.

However, the transconductance Gm is a function of a biasing current of the comparator 110. At start-up, when the biasing current may be very low and below a normal operational level, the transconductance Gm may be close to or equal to zero.

This implies that an output voltage VX at the first node 120 is not defined by error current IP−IN, since this error current is approximately zero. The output voltage may in such case instead be defined by a small difference between resistances RP and RN. If the resistance RP at a certain (low) level of the supply voltage is smaller than RN, the output voltage at the first node 120 could rise and become high, which may incorrectly generate the POR trigger signal.

The trust unit 140 comprises a second output part 144 forming a replica of the first output part 118. The trust unit 140 may further comprise a second transconductor part 142.

The second output part 144 may comprise a second node 146, which similar to the first node 120 of the first output part 118, may be connected to the supply voltage via a third component 148 having the first resistance RP. The third component 148 may be formed by one or more transistors in a manner replicating the first component 122. The second node 146 may further be connected to ground via a second component 150 having the second resistance RN. The fourth component 150 may be formed by one or more transistors in a manner replicating the second component 124.

The second node 146 may be connected to the second transconductor part 142 at a negative side of the second node 146 (at a side connected to ground) forming an unbalanced input to the second output part 144. The second transconductor part 142 may be configured to provide a negative current I_TR to the second node 146. For instance, the second transconductor part 142 may be connected to ground at a positive input and connected to supply voltage at a negative input and may be configured to provide an output based on comparing the positive and negative input. This implies that, when the supply voltage has reached the target voltage level, an output voltage VY at the second node 146 will be low, i.e., opposite to the output voltage VX at the first node 120 which in this case will be high. This may be used for generating a trust signal that is high to the decision unit 130.

At start-up, when the biasing current may be very low and below a normal operational level, the output voltage VY at the second node 146 may, like the first node 120, be defined by a small difference between resistances RP and RN. If there is an unbalance between RP and RN, this will affect the output voltage VY at the second node 146 in a similar manner as affecting the output voltage VX at the first node 120. Further, an absolute value of the negative current I_TR away from the second node 146 will be larger than an absolute value of IN−IP, since there will be a maximum unbalance to the second node 146 because of an absence of any positive current to the second node 146. This implies that the output voltage VY will be high if the output voltage VX is high for low voltage levels of the supply voltage.

Hence, the output voltage VY at the second node 146 of the trust unit 140 may be high if the output voltage VX at the first node 120 of the comparator 110 is high for low levels of the supply voltage, whereas the output voltage VY at the second node 146 of the trust unit 140 may be low if the output voltage VX at the first node 120 of the comparator 110 is high when the supply voltage has reached the target voltage level. This implies that the trust signal from the trust unit 140 may have different value (low/high) for incorrect versus correct indication by the comparator 110 that the supply voltage has reached the target voltage level. This may be utilized such that the trust signal can control that the POR signal is only output when the POR trigger signal is a true indication that the supply voltage has reached the target voltage level.

The comparator 110 and the trust unit 140 are arranged in a common integrated circuit. Preferably, the comparator 110 and the trust unit 140 are arranged closely together in the integrated circuit. This implies that the second output part 144 forming a replica of the first output part 118 exhibits same characteristics as the first output part 118. The second output part 144 and the first output part 118 may be formed by identical components having the same characteristics. Thus, process, voltage, and temperature variations of the components in relation to each other are minimal. This means that the second output part 144 may be relied on to have the same unbalance between RP and RN as the first output part 118 such that the trust unit 140 may be used for identifying when the POR trigger signal is incorrectly output by the comparator 110. Therefore, the trust signal represents an indication whether the POR trigger signal is a trustable representation of the supply voltage reaching the target voltage level.

The decision unit 130 is configured to receive the POR trigger signal and the trust signal and is configured to output the POR signal based on the POR trigger signal and the trust signal. The decision unit 130 may be formed by a single logic gate.

The logic gate of the decision unit 130 may be selected depending on levels (high/low) of the signals from the comparator 110 and the trust unit 140. Or viewed differently, the comparator 110 and the trust unit 140 may be controlled to output levels of the POR trigger signal and the trust signal, respectively, to fit the logic gate used in the decision unit 130.

For instance, the decision unit 130 may be an AND gate, as illustrated in FIG. 2. The decision unit 130 may thus be configured to output the POR signal upon receiving a POR trigger signal that is high and a trust signal that is also high. However, it should be realized that the decision unit 130 may alternatively be a NOR gate. The decision unit 130 may thus be configured to output the POR signal upon receiving a POR trigger signal that is low and a trust signal that is also low.

As described above, the comparator 110 may be configured to provide an output voltage VX that is high when the POR trigger signal is generated. This is suitable for providing the POR trigger signal to the AND gate of the decision unit 130.

However, the first output part 118 may be configured to output a signal via inverters 126a-b of the comparator 110 before the POR trigger signal is output to the decision unit 130. In order to provide a POR trigger signal that is high to the decision unit when the output voltage VX is high, an even number of inverters 126*a-b* should be used.

The inverters 126*a-b* may be useful in regenerating a level of the output voltage, wherein a size of the inverters 126*a-b* is increasing towards the output to the decision unit 130. Having a plurality of inverters 126*a-b* may be advantageous in that the first inverters (close to the first node 120) will not consume much current even if receiving an input at mid-supply. This is useful as the POR circuitry 100 may change state slowly.

As described above, the trust unit 140 may be configured to provide an output voltage VY that is low when the POR trigger signal may be trusted and is high when the POR trigger signal is incorrectly generated for low supply voltages. Thus, the output voltage VY needs to be inverted for providing the trust signal to the AND gate of the decision unit 130.

Therefore, the second output part 144 may be configured to output a signal via at least one inverter 152 of the trust unit 140 before the trust signal is output to the decision unit 130. In order to provide a trust signal that is high to the decision unit when the output voltage VY is low (and the POR trigger signal can be trusted), an odd number of inverters 152 should be used.

The at least one inverter 152 is further beneficial for ensuring a low current consumption as described above for the comparator 110. Also, the inverters 126*a-b* and 152 are advantageous in decoupling input to the AND gate from the second output part 144. The second output part 144 does not consume much power and therefore has very high impedance. If the trust signal would be provided directly from the second node 146 to the AND gate, when the comparator 110 flips, capacitively some charge could get into the second node 120 and cause the trust unit 140 to change its state. This would imply that the trust signal could turn low and, hence, the POR signal would not be correctly output by the decision unit 130.

If the decision unit 130 is a NOR gate instead of an AND gate, the comparator 110 may comprise an odd number of inverters and the trust unit 140 may comprise an even number of inverters to ensure that the POR trigger signal and the trust signal are low when the supply voltage has reached the target level.

Figure 3:
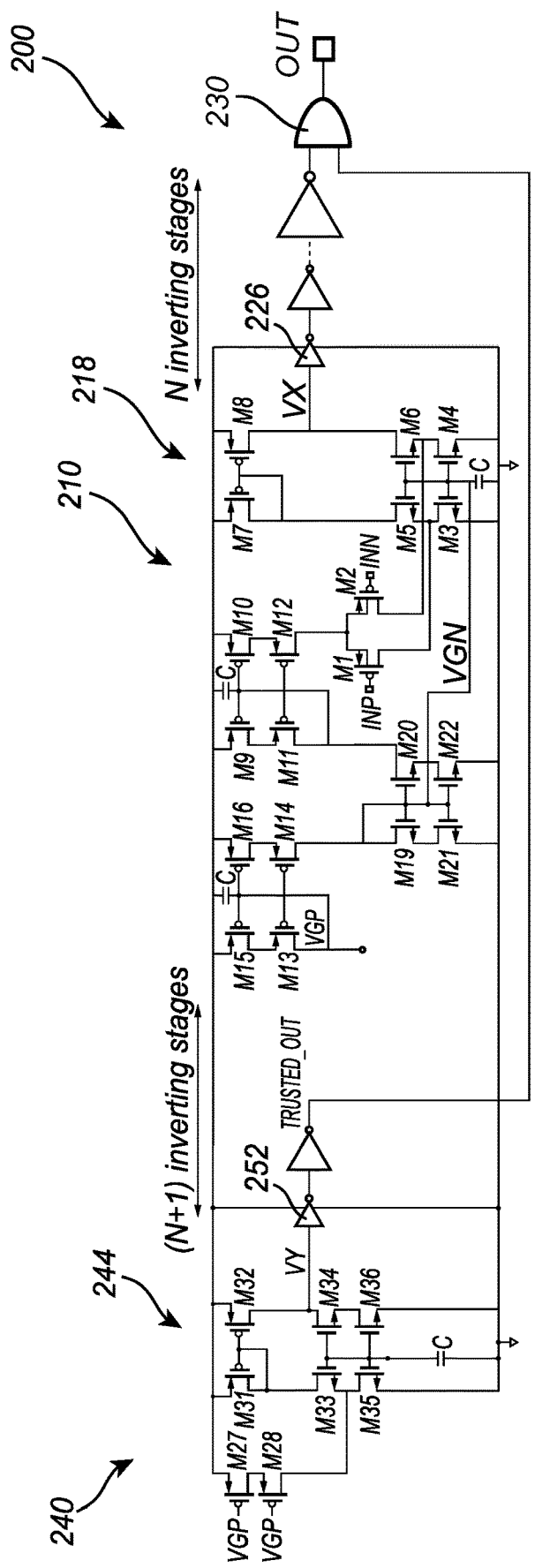
FIG. 3 is a circuit diagram representation of an exemplary POR circuitry.

Referring now to FIG. 3, an example of an implementation of the POR circuitry 200 is illustrated.

The POR circuitry 200 comprises a comparator 210 implemented by transistors M1-M22 having a self-biased folded cascode. The comparator 210 comprises a first output part 218 implemented by transistors M3-M8.

The trust unit 240 is implemented by transistors M27-M28 and M31-M36, wherein the second output part 244 is formed by transistors M31-M36. As may be seen in FIG. 3, the second output part 244 is a replica of the first output part 218.

In normal operating conditions, when a bias current and the supply voltage are at target levels, a current flowing via M27-M28 will unbalance the second output part 244 such that the output voltage VY will be low. As indicated in FIG. 3, the trust unit 240 comprises N+1 inverting stages 252, where N is an even integer number, such that the inverting stages 252 will invert the output voltage VY to a high trust signal when the bias current and the supply voltage are at target levels.

At start-up, the voltage VGP provided to gate of transistors will be close to supply voltage, because of bias current being low. This implies that drain current of M27 will be almost zero. Further, drain currents of M1 and M2 flowing in the comparator 210 will also be almost zero. Thus, the first output part 218 and the second output part 244 will behave in same manner. If the output voltage VX is high such that the POR trigger signal is high, the output voltage VY will in this case also be high. Thanks to the inverting stages 226, 252 of the comparator 210 and the trust unit 240 being an even number and an odd number, respectively, the AND gate of the decision unit 230 will receive a trust signal that is low such that the POR signal will not be incorrectly generated.

Figure 4:
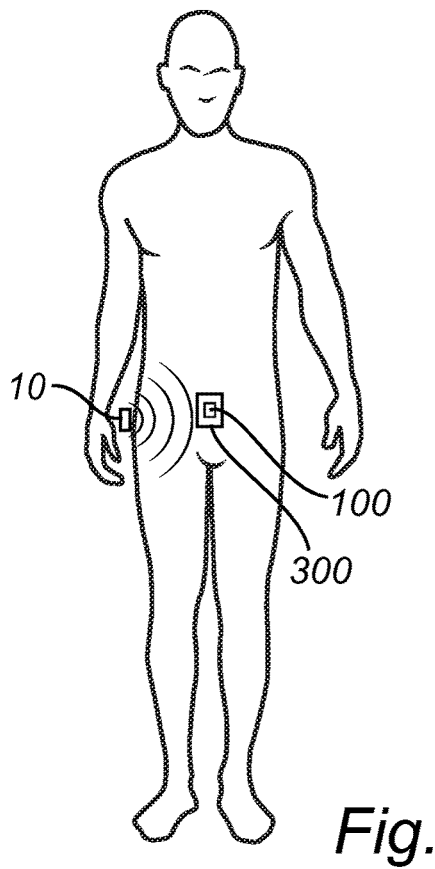
FIG. 4 is a schematic view of an implant device according to an embodiment.

Referring now to FIG. 4, the POR circuitry 100 (such as the detailed example of the POR circuitry 200 shown in FIG. 3) may be advantageously provided in an implant device 300. Although it should be realized that the POR circuitry 100 may be provided for use controlling a power-on reset signal in any device, the POR circuitry 100 is particularly suited for use in the implant device 300, as the POR circuitry 100 is adapted to provide a reliable POR signal when the supply voltage rises slowly or unpredictably. This may typically be the case for the implant device 300 which may be powered through wireless power transfer that may be subject to dynamically changing conditions.

The implant device 300 may be configured to be implanted in a human body or an animal body and may need wireless power transfer for powering the implant device 300 while being implanted. For instance, the implant device 300 may receive power from a power transmitter 10, which may be arranged externally to the human body or animal body.

Thanks to using the POR circuitry 100 in the implant device 300, the POR signal may be generated in a reliable manner to ensure a proper functionality of the implant device 300 even though the settling time of the supply voltage during start-up may vary between different start-up occasions.

Figure 5:
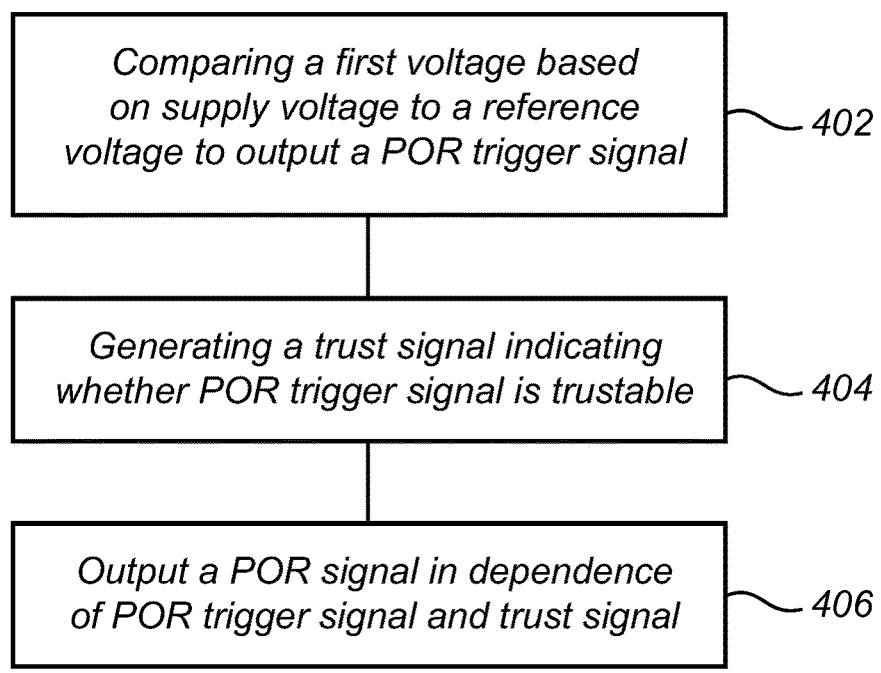
FIG. 5 is a flow chart of a method.

Referring now to FIG. 5, a method for generating a POR signal will be described.

The method comprises comparing 402, by the comparator 110, a first voltage based on supply voltage and a reference voltage to output a POR trigger signal in dependence of a target voltage level of the supply voltage. The comparator 110 comprises the first output part 118 configured to receive a balanced input from the first transconductor part 112.

The method further comprises generating 404, by the trust unit 140, a trust signal representing an indication whether the POR trigger signal is a trustable representation of the supply voltage reaching the target voltage level. The trust unit 140 comprises a second output part 144 forming a replica of the first output part 118 and configured to receive an unbalanced input. The trust unit 140 may be configured to ensure that the trust signal indicates that the POR trigger signal cannot be trusted, when the POR trigger signal is incorrectly generated due to an unbalance of the first output part 118 that may cause output of the POR trigger signal when supply voltage is low.

The method further comprises outputting 406, by the decision unit 130, a POR signal in dependence of the POR trigger signal and the trust signal. In this manner, the method provides reliable output of the POR signal when the supply voltage has reached the target voltage level.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A power-on reset (POR) circuitry comprising:
a comparator configured to compare a first voltage to a reference voltage based on a supply voltage, wherein the comparator is configured to output a POR trigger signal in dependence of a relation between the supply voltage and a target voltage level, wherein the comparator comprises a first output part configured to receive a balanced input, the first output part having a first component with a first resistance and a second component with a second resistance between the supply voltage and ground;
a trust unit comprising a second output part that is a replica of the first output part and is configured to receive an unbalanced input, the second output part having another first component and another second component between the supply voltage and ground, wherein the comparator and the trust unit are arranged in a common integrated circuit, and wherein the trust unit is configured to output a trust signal representing an indication whether the POR trigger signal is a trustable representation of the supply voltage reaching the target voltage level; and
a decision unit configured to receive the POR trigger signal and the trust signal and configured to output a POR signal in dependence of the POR trigger signal and the trust signal.

2. The POR circuitry according to claim 1, wherein the comparator further comprises a first input transconductor part configured to generate a current to the first output part.

3. The POR circuitry according to claim 2, wherein the first input transconductor part is configured to receive the first voltage and the reference voltage as input signals to the comparator.

4. The POR circuitry according to claim 1, wherein the trust unit comprises a second transconductor part at a negative side of the unbalanced input.

5. The POR circuitry according to claim 4, wherein the second transconductor part is configured to receive the supply voltage at a negative input and ground at a positive input.

6. The POR circuitry according to claim 1, wherein the first output part is configured to output a signal to at least one inverter of the comparator, wherein the comparator is configured to output the POR trigger signal from the at least one inverter of the comparator.

7. The POR circuitry according to claim 6, wherein the second output part is configured to output a signal to at least one inverter of the trust unit, wherein the trust unit is configured to output the trust signal from the at least one inverter of the trust unit.

8. The POR circuitry according to claim 7, wherein a number of inverters of the at least one inverter of the comparator is even and a number of inverters of the at least one inverter of the trust unit is odd or the number of inverters of the at least one inverter of the comparator is odd and the number of inverters of the at least one inverter of the trust unit is even.

9. The POR circuitry according to claim 8, wherein the decision unit comprises an AND gate or a NOR gate configured to receive the POR trigger signal and the trust signal and configured to output the POR signal.

10. The POR circuitry according to claim 1, wherein the first component includes one or more transistors having the first resistance, wherein the first component is connected between an output node of the first output part and the supply voltage.

11. The POR circuitry according to claim 10, wherein the another first component includes one or more transistors having the first resistance, wherein the another first component is connected between an output node of the second output part and the supply voltage.

12. The POR circuitry according to claim 1, wherein the second component includes one or more transistors having the second resistance, wherein the second component is connected between an output node of the first output part and ground.

13. The POR circuitry according to claim 12, wherein the another second component includes one or more transistors having the second resistance, wherein the another second component is connected between an output node of the second output part and ground.

14. An implant device comprising:
a power-on reset (POR) circuitry comprising:
a comparator configured to compare a first voltage to a reference voltage based on a supply voltage, wherein the comparator is configured to output a POR trigger signal in dependence on a relation between the supply voltage and a target voltage level, wherein the comparator comprises a first output part configured to receive a balanced input, the first output part having a first component with a first resistance and a second component with a second resistance between the supply voltage and ground;
a trust unit comprising a second output part that is a replica of the first output part and is configured to receive an unbalanced input, the second output part having another first component and another second component between the supply voltage and ground, wherein the comparator and the trust unit are arranged in a common integrated circuit and wherein the trust unit is configured to output a trust signal representing an indication whether the POR trigger signal is a trustable representation of the supply voltage reaching the target voltage level; and
a decision unit configured to receive the POR trigger signal and the trust signal and configured to output a POR signal in dependence of the POR trigger signal and the trust signal wherein the implant device is configured to be implanted in a body and is configured to receive power through wireless power transfer for causing generation of the POR signal by the POR circuitry.

15. A method for generating a power-on reset (POR) signal, comprising:
comparing, by a comparator, a first voltage to a reference voltage based on a supply voltage to output a POR trigger signal in dependence on a relation between the supply voltage and a target voltage level, wherein the comparator comprises a first output part configured to receive a balanced input, the first output part having a first component with a first resistance and a second component with a second resistance between the supply voltage and ground;
generating, by a trust unit, a trust signal representing an indication whether the POR trigger signal is a trustable representation of the supply voltage reaching the target voltage level, wherein the trust unit comprises a second output part that is a replica of the first output part and is configured to receive an unbalanced input, the second output part having another first component and another second component between the supply voltage and ground, wherein the comparator and the trust unit are arranged in a common integrated circuit; and outputting, by a decision unit, a POR signal in dependence of the POR trigger signal and the trust signal.

* * * * *